United States Patent
Tanaka et al.

(10) Patent No.: US 9,449,388 B2
(45) Date of Patent: Sep. 20, 2016

(54) MEASUREMENT APPARATUS, PROGRAM, AND MEASUREMENT METHOD

(71) Applicant: Sony Corporation, Tokyo (JP)

(72) Inventors: Eiichi Tanaka, Chiba (JP); Masanobu Tamai, Chiba (JP); Hiroaki Morikawa, Kanagawa (JP); Hirokazu Tatsuta, Tokyo (JP); Suguru Dowaki, Kanagawa (JP); Tomohiro Hayakawa, Saitama (JP); Eriko Matsui, Tokyo (JP); Shin Hasegawa, Kanagawa (JP); Tatsuya Minakawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 56 days.

(21) Appl. No.: 14/371,015

(22) PCT Filed: Jan. 8, 2013

(86) PCT No.: PCT/JP2013/000019
§ 371 (c)(1),
(2) Date: Jul. 8, 2014

(87) PCT Pub. No.: WO2013/105485
PCT Pub. Date: Jul. 18, 2013

(65) Prior Publication Data
US 2014/0348411 A1 Nov. 27, 2014

(30) Foreign Application Priority Data
Jan. 13, 2012 (JP) ................. 2012-005682

(51) Int. Cl.
*G06T 7/00* (2006.01)
*G01N 35/00* (2006.01)
*G06T 7/20* (2006.01)

(52) U.S. Cl.
CPC ......... *G06T 7/0016* (2013.01); *G01N 35/0099* (2013.01); *G01N 35/00603* (2013.01); *G06T 7/20* (2013.01); *G06T 2207/10056* (2013.01); *G06T 2207/30004* (2013.01)

(58) Field of Classification Search
None
See application file for complete search history.

(56) References Cited

U.S. PATENT DOCUMENTS 6,631,331 B1 *  10/2003  Sabry ................. G06K 9/00127
                                                  318/640
8,859,263 B2 *  10/2014  Greenberger .......... C12M 23/12
                                                  359/395

(Continued)

FOREIGN PATENT DOCUMENTS

| JP | 62-237342   | 10/1987 |
| JP | 2008-289799 | 12/2008 |
| JP | 2010-130966 | 6/2010  |

OTHER PUBLICATIONS

International Search Report issued in connection with International Application No. PCT/JP2013/000019, dated May 10, 2013. (3 pages).

Primary Examiner — Bhavesh Mehta
Assistant Examiner — Narek Zohrabyan
(74) Attorney, Agent, or Firm — Chip Law Group

(57) ABSTRACT

There is provided a measurement apparatus including an objective lens, a stage, a setting unit, and a controller. The stage is configured to support a sample vessel in which a plurality of wells each containing a sample are arranged and to define relative positions of the sample vessel and the objective lens. The setting unit is configured to determine whether to set each of the plurality of wells to be a measurement target and set the measurement target. The controller is configured to control the stage such that a well determined to be the measurement target by the setting unit and the objective lens face each other.

14 Claims, 7 Drawing Sheets

(56) References Cited

U.S. PATENT DOCUMENTS

| | | | |
|---|---|---|---|
| 2003/0040031 A1* | 2/2003 | Kim | B01L 3/5025 435/29 |
| 2003/0185450 A1* | 10/2003 | Garakani | G06K 9/0014 382/232 |
| 2004/0102742 A1 | 5/2004 | Tuyl | |
| 2004/0109593 A1* | 6/2004 | Jung | G01N 15/1468 382/128 |
| 2006/0068377 A1* | 3/2006 | Tsipouras | G01N 1/312 435/4 |
| 2006/0275745 A1* | 12/2006 | Schwarz | G06K 9/0014 435/4 |
| 2007/0064101 A1* | 3/2007 | Hasegawa | G02B 21/367 348/79 |
| 2009/0046359 A1* | 2/2009 | Kiyota | G02B 21/367 359/383 |
| 2014/0106389 A1* | 4/2014 | Loewke | G02B 21/0088 435/29 |
| 2014/0152798 A1* | 6/2014 | Kataoka | G01N 21/6452 348/79 |
| 2015/0278625 A1* | 10/2015 | Finkbeiner | G02B 21/26 348/79 |

* cited by examiner

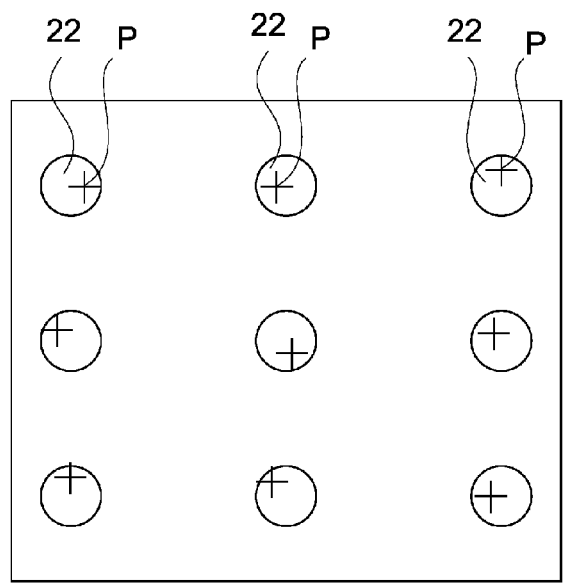
FIG.4
FIG.5
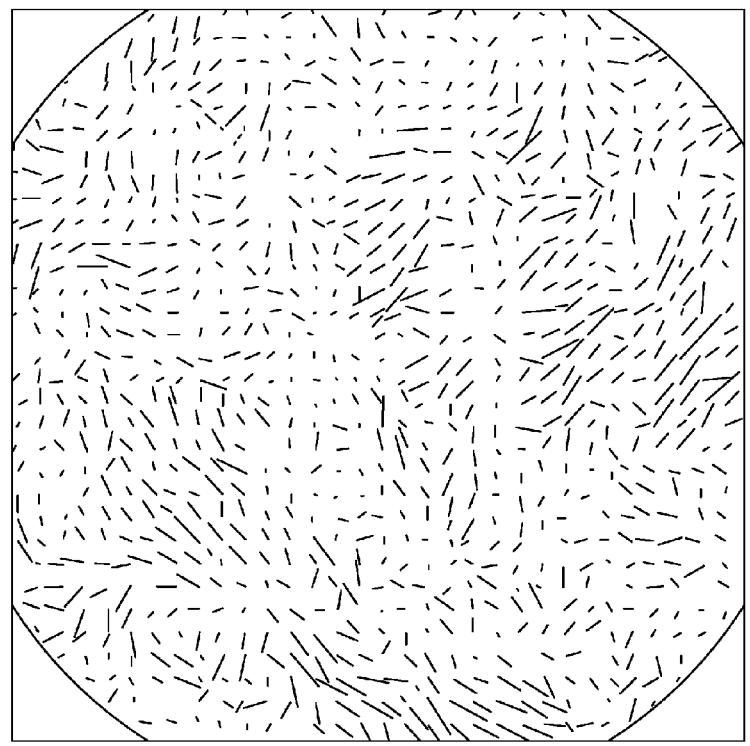

MEASUREMENT APPARATUS, PROGRAM, AND MEASUREMENT METHOD

CROSS REFERENCES TO RELATED APPLICATIONS

The present application is a national stage of International Application No. PCT/JP2013/000019 filed on Jan. 8, 2013 and claims priority to Japanese Patent Application No. 2012-005682 filed on Jan. 13, 2012, the disclosure of which is incorporated herein by reference.

BACKGROUND

The present disclosure relates to a measurement apparatus that measures samples contained in a plurality of wells by a microscope, and to a program and a measurement method therefor.

In the field of a pathological diagnosis and the like, in the case of measuring a sample that generates pulsations, such as a myocardial cell, image analysis may be performed on images of the sample magnified by a microscope. This is because the image analysis allows a movement of the sample to be observed with the elapse of time by comparing images captured at different times of day.

CITATION LIST

Patent Literature

[PTL 1]
Japanese Patent Application Laid-open No. 2008-289799
[PTL 2]
Japanese Patent Application Laid-open No. 2010-130966

SUMMARY

Technical Problem

Image analysis is performed on images of a sample magnified by a microscope to measure a sample that generates pulsations. For example, Patent Literature 1 discloses a cardiac function analyzing apparatus that analyzes a cardiac motion by image analysis. The cardiac function analyzing apparatus is configured to obtain the positions of anatomically corresponding points of a heart in images obtained by imaging the heart, thus calculating displacements of the points with the elapse of time. The cardiac function analyzing apparatus can display the movements of the respective points so as to meet the shape of the heart.

Further, Patent Literature 2 discloses a myocardial toxicity examining apparatus capable of performing image analysis in a laboratory system (in vitro system). The myocardial toxicity examining apparatus can evaluate the influence of a medicine on a myocardial cell by forming a cell network on a substrate, administering the medicine thereto, and detecting pulsations of a myocardial cell by image analysis.

As described above, the measurement apparatus that deals with a sample that generates pulsations, such as a myocardial cell, generally images the sample over a predetermined period of time (captures moving images or still images) to detect a movement of the sample based on the change of the images due to times of day. Therefore, it is necessary to eliminate vibrations of the measurement apparatus during measurement to extract only the change of the images due to pulsations.

A sample is generally contained in a section called well together with a culture solution. In general, a plurality of samples are measured collectively, and therefore a plurality of wells are provided. Here, there may be samples that are unsuitable for measurement among the samples contained in the plurality of wells. For example, such samples may be pulsatile cells whose pulsations are already stopped. The measurement of those wells is waste of time, and there arises a demand for improvement in such a case.

In view of the circumstances as described above, it is desirable to provide a measurement apparatus, a program, and a measurement method that are suitable for measurement of samples contained in a plurality of wells over a predetermined period of time by using a microscope.

Solution to Problem

According to an embodiment of the present disclosure, there is provided a measuring apparatus including a stage configured to support a vessel including a plurality of samples, each of the samples contained within a respective well. The measuring apparatus also includes an image device configured to capture an image of at least one sample and a processor communicatively coupled to a stage controller and configured to determine which of the plurality of samples are to be imaged and which of the plurality of samples are not to be imaged.

According to another embodiment of the present disclosure, there is provided a measurement apparatus including an objective lens, a stage, a setting unit, and a controller. The stage is configured to support a sample vessel in which a plurality of wells each containing a sample are arranged and to define relative positions of the sample vessel and the objective lens. The setting unit is configured to determine whether to set each of the plurality of wells to be a measurement target and set the measurement target. The controller is configured to control the stage such that a well determined to be the measurement target by the setting unit and the objective lens face each other.

With this configuration, the setting unit determines whether to set each of the plurality of wells to be a measurement target and sets the measurement target, with the result that the controller can control the stage so as to operate only for the well that has been determined to be the measurement target. Therefore, the measurement is not performed on wells that have not been determined to be measurement targets, which leads to the shortening of the whole measurement time.

The measurement apparatus may further include a coordinate acquisition unit configured to acquire coordinates of positions of the stage at which each of the plurality of wells faces the objective lens at an observation position thereof. The setting unit may be configured to supply, of the coordinates of the positions of the stage, coordinates of a position at which a well determined to be the measurement target faces the objective lens at an observation position thereof, to the controller.

With this configuration, the controller can move the stage to the coordinates of the position at which the well determined to be the measurement target and the objective lens face each other to thereby perform measurement.

The coordinate acquisition unit may be configured to acquire coordinates of positions of the stage at which each of the plurality of wells faces the objective lens at a center position thereof, and the controller may control the stage such that each of the plurality of wells faces the objective lens at the center position thereof.

With this configuration, since the stage is moved by the controller such that each of the plurality of wells faces the objective lens at the center position thereof, it is not necessary to adjust the position of the stage such that each well falls within the field of view when the user determines an observation position of an image of each well. Therefore, the user can determine the observation position speedily, which leads to the shortening of the whole measurement time.

The coordinate acquisition unit may be configured to acquire, based on coordinates of positions of the stage at which each of wells at four corners of the sample vessel faces the objective lens at a center position thereof, the wells being designated by a user, and on an array of the plurality of wells in the sample vessel, the coordinates of the positions of the stage at which each of the plurality of wells faces the objective lens at the center position thereof.

The setting unit may be configured to perform the setting based on a result of image analysis of the sample, the result being imaged via the objective lens.

With this configuration, it is possible to automatically determine a well that is not determined to be a measurement target by the setting unit based on the result of the image analysis of the sample, for example, on the level of the pulsations of the sample.

The sample may include a pulsatile cell, and the setting unit may be configured to exclude, from measurement targets, a well containing a pulsatile cell whose pulsations are stopped.

As described above, when the pulsatile cell is used as a sample to measure its pulsations, it is not necessary to measure a sample whose pulsations are stopped. With this configuration, a sample whose pulsations are already stopped can be prevented from being measured.

The measurement apparatus may further include a vibration isolation table including the objective lens and the stage and being configured to attenuate vibrations from the outside.

With this configuration, it is possible to remove, by the vibration isolation table, vibrations applied to the measurement apparatus from the outside and prevent the reduction in measurement precision due to the influence of the vibrations when the pulsations of a cell is measured over a predetermined period of time.

According to another embodiment of the present disclosure, there is provided a program causing a computer to function as a setting unit and a controller. The setting unit is configured to determine whether to set each of a plurality of wells to be a measurement target and set the measurement target in a sample vessel in which the plurality of wells each containing a sample are arranged. The controller is configured to control a stage configured to support the sample vessel such that a well determined to be the measurement target by the setting unit and an objective lens face each other.

According to another embodiment of the present disclosure, there is provided a measurement method including: determining, by a setting unit, whether to set each of a plurality of wells to be a measurement target and setting the measurement target in a sample vessel in which the plurality of wells each containing a sample are arranged; and controlling, by a controller, a stage configured to support the sample vessel such that a well determined to be the measurement target by the setting unit and an objective lens face each other.

Advantageous Effect of Invention

As described above, according to the embodiments of the present disclosure, it is possible to provide a measurement apparatus, a program, and a measurement method that are suitable for measurement of samples contained in a plurality of wells over a predetermined period of time by using a microscope.

Additional features and advantages are described herein, and will be apparent from the following Detailed Description and the figures.

BRIEF DESCRIPTION OF THE FIGURES

FIG. 4 is a schematic diagram showing an observation position in each well.

FIG. 5 is a diagram showing an example of results of image analysis performed by the measurement apparatus.

DETAILED DESCRIPTION (First Embodiment)

Hereinafter, a measurement apparatus according to a first embodiment will be described.

(Configuration of Measurement Apparatus)

Figure 1:
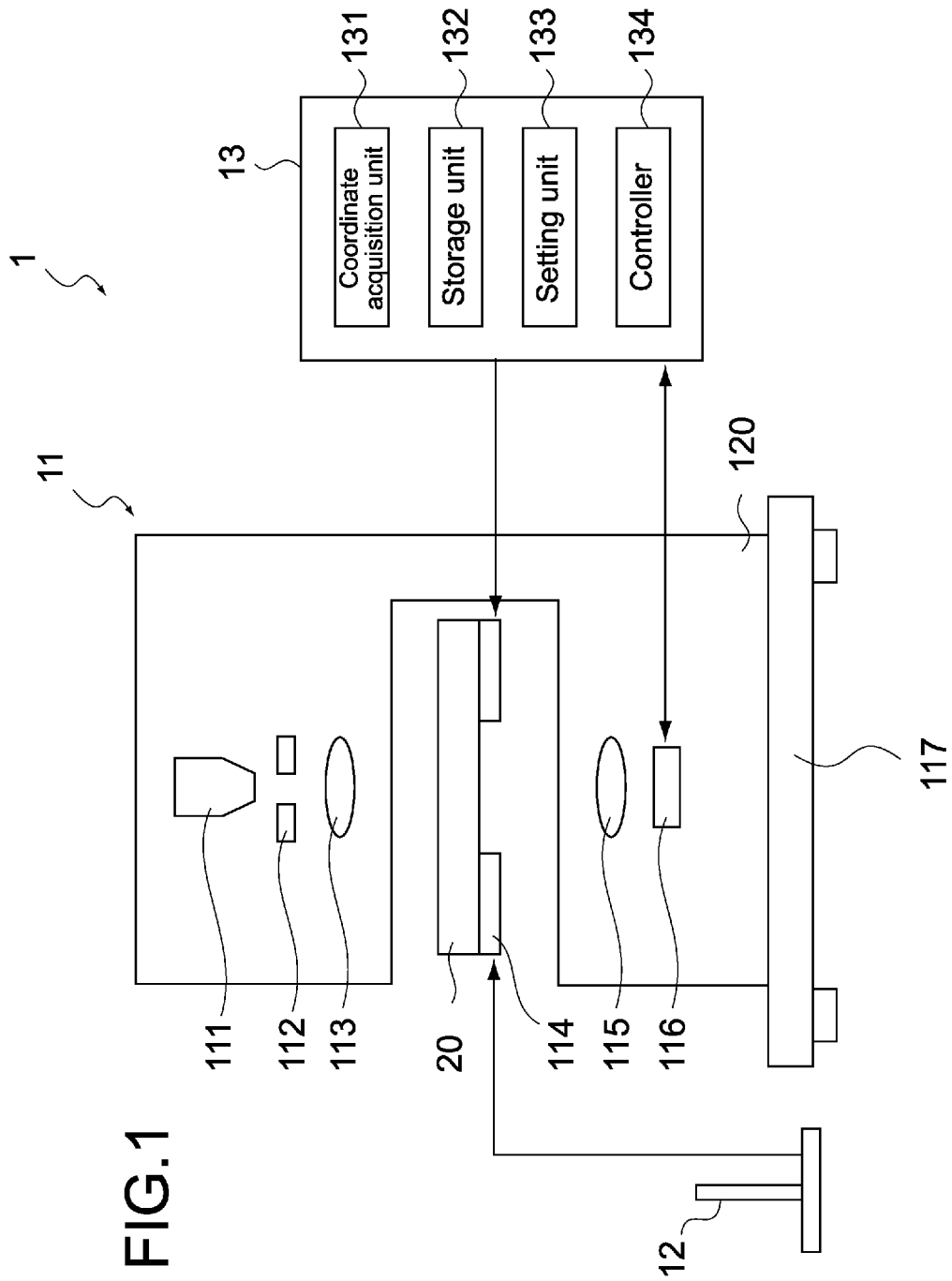
FIG. 1 is a schematic diagram showing the configuration of a measurement apparatus according to a first embodiment and a second embodiment.

FIG. 1 is a schematic diagram showing the configuration of a measurement apparatus 1. As shown in FIG. 1, the measurement apparatus 1 includes a main body 11, a stage controller 12, and a PC (Personal Computer) 13. The main body 11 may be a phase-contrast microscope. It should be noted that such a configuration is merely an example, and the configuration corresponding to the stage controller 12 and the PC 13 may be provided to the main body 11.

In the main body 11, the casing 120 houses an illumination light source 111, a ring aperture 112, a condenser lens 113, a stage 114, an objective lens 115, and an imaging device 116 and is mounted on a vibration isolation table 117. The culture vessel 20 in which a sample is contained is mounted on the stage 114.

The illumination light source 111 is a light source that irradiates the culture vessel 20 with illumination light, for example, visible light or excitation light. The illumination light source 111 may be an LED (Light Emitting Diode) and the like. The ring aperture 112 is an aperture for adjusting the amount of illumination light emitted from the illumination light source 111. The condenser lens 113 is a lens for condensing the illumination light having passed through the ring aperture 112 to the culture vessel 20. The configuration of the illumination light source 111, the ring aperture 112, and the condenser lens 113 may be changed as appropriate.

The stage 114 supports the culture vessel 20 and defines relative positions of the culture vessel 20 and the objective lens 115. Specifically, the stage 114 is configured to be three-dimensionally movable with respect to the casing 120 provided with the objective lens 115 and is movable on an X-Y plane (plane parallel to a mounting surface of the stage) and in a Z direction (direction vertical to the mounting surface of the stage). The stage 114 is connected to the stage controller 12 and is configured to move in accordance with the operation of the stage controller 12 by the user.

The objective lens 115 magnifies the light having been emitted from the illumination light source 111 and having passed through the sample at a predetermined magnification, and condenses the light to the imaging device 116. The objective lens 115 may be, for example, an objective lens incorporating a phase difference ring. The imaging device 116 is an imaging device capable of capturing a moving image and may be a CCD (Charge Coupled Device), a CMOS (Complementary Metal Oxide Semiconductor), and the like. The imaging device 116 is connected to the PC 13 and is configured to output a captured image (moving image) to the PC 13.

The vibration isolation table 117 supports the casing 120 and attenuates vibrations of an outer portion (mounting surface). A vibration isolation table for a microscope that is capable of coping with micro vibrations is suitable for the vibration isolation table 117. The main body 11 has the configuration as described above. The main body 11 may have an alternate or additional configuration in addition to the configurations used herein and may include an eyepiece lens, for example.

Figure 2:
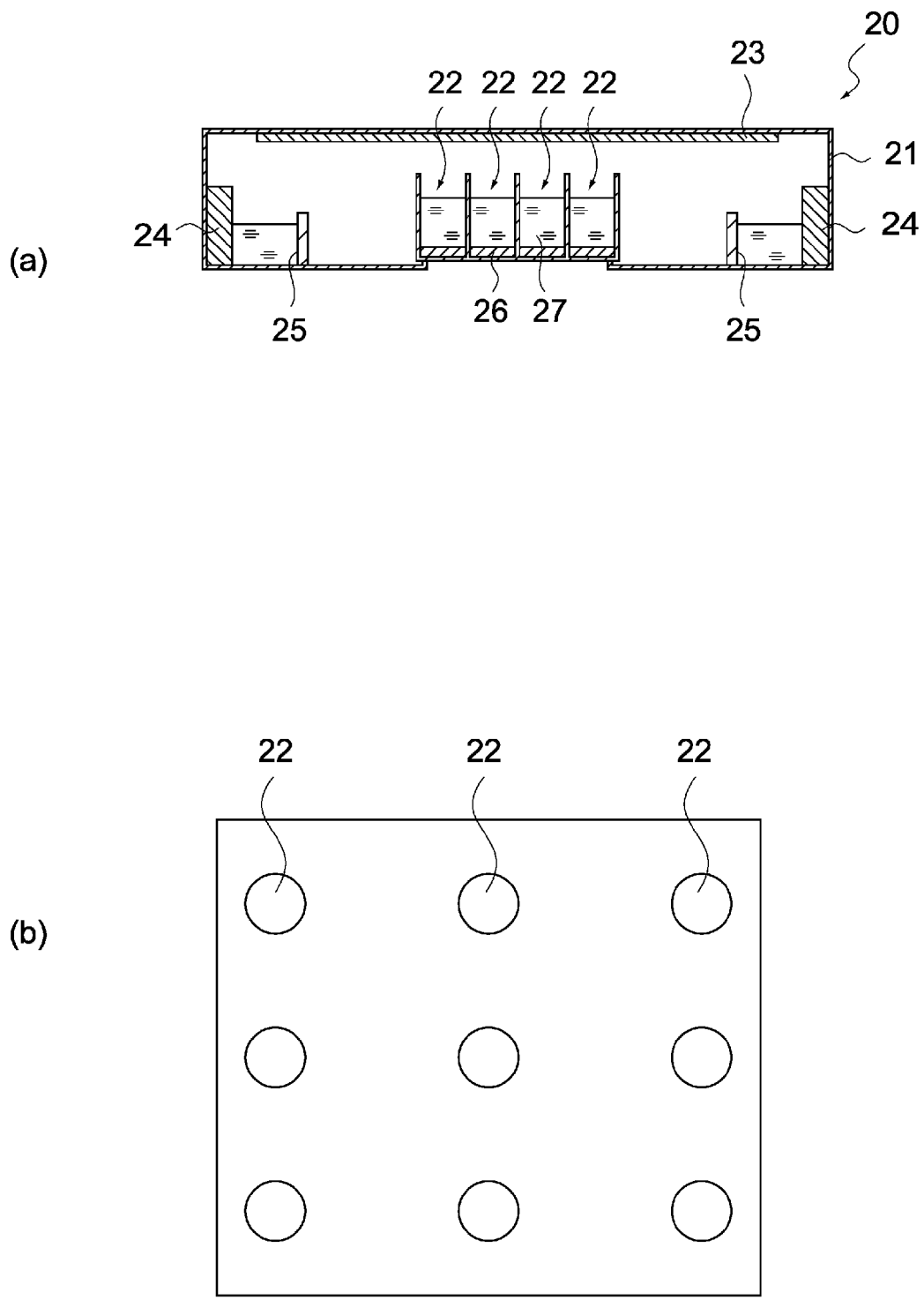
FIGS. 2A and 2B are schematic views each showing the configuration of a culture vessel mounted to the measurement apparatus.

The culture vessel 20 can have a plurality of wells (sections in which samples are contained) arranged along the X-Y plane. FIG. 2 are schematic views each showing the culture vessel 20. FIG. 2A is a cross-sectional view of the culture vessel 20, and FIG. 2B is a plan view of the culture vessel 20.

As shown in FIG. 2A, the culture vessel 20 includes a culture chamber 21, wells 22, a glass heater 23, heaters 24, and a tank 25. Each of the wells 22 contains a sample 26 and a culture solution 27.

The culture chamber 21 is a chamber capable of keeping its inside airtight and houses the wells 22, the glass heater 23, the heaters 24, and the tank 25. Each of the wells 22 is a section partitioned by partition walls and capable of retaining liquid. As shown in FIG. 2B, a plurality of wells 22 are arranged in a matrix. FIGS. 2A and 2B show a small number of wells 22, but a larger number of wells 22, for example, 96 wells 22 or 48 wells 22 are provided in reality.

The glass heater 23 and the heaters 24 are heaters for keeping predetermined temperature, for example, temperature suitable for the cultivation of cells, in the culture chamber 21. The glass heater 23 has light transparency in order to transmit illumination light. The tank 25 is provided on the inner circumference of the culture chamber 21 and is configured to retain water used for keeping predetermined humidity in the culture chamber 21.

The samples 26 are contained in the respective wells 22. Though not particularly limited, the samples 26 may be pulsatile cells, for example, myocardial cells. The culture solution 27 is for cultivating the samples 26 and is appropriately selected in accordance with the types of samples 26.

The culture chamber 21 can be filled with a cultivation gas suitable for cultivation of the samples 26. The cultivation gas may be, for example, air having a temperature of 37° C. and containing 5 to 7% of $CO_2$.

The culture vessel 20 can be configured as described above. The illumination light coming from the condenser lens 113 passes through the culture chamber 21 and the glass heater 23 and enters one of the wells 22. The illumination light passes through the culture solution 27 and the sample 26 and is emitted from the bottom surface of the well 22 to reach the objective lens 115. The replacement of the sample 26 and the culture solution 27 can be performed by removing the glass heater 23.

The stage controller 12 is connected to the stage 114 and is configured to move the stage 114 in the X-Y plane direction and in the Z direction upon reception of an operation by the user. Any stage controller may be used as the stage controller 12.

The PC 13 is constructed by cooperation of software and hardware such as a processor, a memory, and storage and may have the configuration as shown in FIG. 1. Specifically, the PC 13 includes a coordinate acquisition unit 131, a storage unit 132, a setting unit 133, and a controller 134.

The coordinate acquisition unit 131 acquires coordinates of the stage 114. Specifically, when the user operates the stage controller 12 to move the stage 114 to coordinates of a predetermined position (hereinafter, referred to also as position coordinates), the coordinate acquisition unit 131 receives an instruction of the user to acquire the position coordinates of the stage 114 at that time. The position coordinates of the stage 114 can be acquired as, for example, numerical values of X, Y, and Z coordinates.

The storage unit 132 stores the position coordinates of the stage 114, which have been acquired by the coordinate acquisition unit 131. The storage unit 132 supplies the position coordinates to the controller 134 in response to a request.

The setting unit 133 determines whether to set each of the plurality of wells 22 to be a measurement target and set the measurement target. The setting unit 133 determines a well 22 unsuitable for measurement by means of the designation by the user, the analysis of captured images (to be described later), or the measurement using electrodes (to be described later). For example, in the case where the sample 26 is a pulsatile cell, the well 22 unsuitable for measurement may be a well 22 containing a pulsatile cell whose pulsations are stopped. Further, the setting unit 23 can set, of the wells 22, the well 22 located at the outer circumference to be a well unsuitable for measurement. This is because the culture solution 27 evaporates faster in the well 22 located at the outer circumference than in the other wells 22.

The controller 134 moves the stage 114 to be located at the position coordinates stored in the storage unit 132 and causes the imaging device 116 to capture an image of the sample 26 (moving image or continuous still images). Upon completion of the imaging, the controller 134 moves the stage 114 to the next position coordinates and causes the imaging device 116 to perform imaging in a repeated manner. In the case where a well 22 that is not determined to be a measurement target is set by the setting unit 133, the controller 134 does not move the stage 114 to position coordinates corresponding to the well 22 and moves the stage 114 to position coordinates of another well 22 as the next measurement target.

The PC 13 may be configured as described above. In addition thereto, it is assumed that the PC 13 is connected with an input interface, a display, and the like (not shown).

(Operation of Measurement Apparatus)

Figure 3:
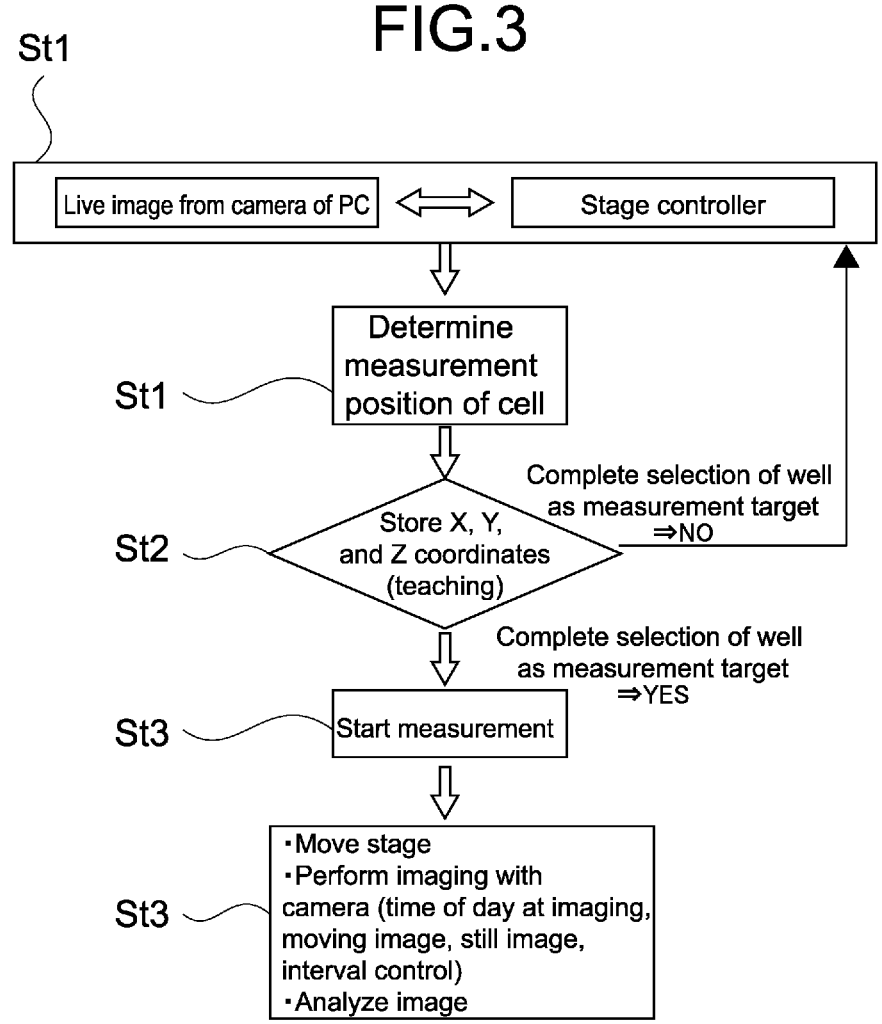
FIG. 3 is a flowchart showing the operation of the measurement apparatus according to the first embodiment.

The operation of the measurement apparatus 1 configured as described above will be described. FIG. 3 is a flowchart showing the operation of the measurement apparatus 1.

First, the user determines an observation position (St 1). Specifically, the user operates the stage controller 12 while viewing a low-magnification image of a partial area in the culture vessel 20, which is displayed on the display of the PC 13, and focuses the field of view on one of the wells 22. Next, the well 22 is magnified and the observation position in the well 22 is determined. For example, in the case where the sample 26 is a pulsatile cell, the observation position may be set to a position where active pulsations are observed. FIG. 4 is a schematic diagram showing an example of observation positions in the respective wells 22 of the culture vessel 20 (observation positions being denoted by P in FIG. 4).

Upon determination of the observation position, the user makes inputs to the PC 13. In response to this, the coordinate acquisition unit 131 acquires position coordinates of the stage 114 at that time and supplies the position coordinates to the storage unit 132 (teaching) (St 2). Subsequently, the user returns the magnification of the image to a lower one and focuses the field of view on the next well 22. Further, the user determines the observation position in the well 22 in the above-mentioned manner and makes inputs to the PC 13. The coordinate acquisition unit 131 acquires position coordinates of the stage 114 at that time in the same manner. After that, the user designates an observation position of each of the wells 22 in the same manner so that the coordinate acquisition unit 131 acquires position coordinates of the stage 114 for each of the wells 22.

Here, in the case where there are wells 22 unsuitable for measurement, such as a well 22 containing a pulsatile cell whose pulsations are stopped, the user can make inputs indicating that the wells 22 are unsuitable for measurement to the PC 13. In response to this, the setting unit 133 can delete the position coordinates corresponding to the wells 22 from the storage unit 132. Further, the setting unit 133 can detect the wells 22 unsuitable for measurement based on results of the image analysis to be described later or the output of electrodes immersed in the wells 22 in addition to the inputs by the user and delete the position coordinates of the wells 22 from the storage unit 132.

Upon completion of the determination of the observation positions for all the wells 22 in the culture vessel 20, the measurement is started (St 3). The controller 134 acquires the position coordinates of the stage 114, which correspond to the wells 22, from the storage unit 132 and moves the stage 114 so as to be positioned at the position coordinates. Upon completion of the movement of the stage 114, the controller 134 causes the imaging device 116 to capture an image (moving image or still image). In this case, the controller 134 may control the illumination light source 111, the ring aperture 112, and the objective lens 115 at the same time and adjust imaging conditions.

Upon completion of the movement of the stage 114 and the imaging by the imaging device 116 for all the position coordinates stored in the storage unit 132, this measurement is terminated. After that, for example, it is also possible to perform the movement of the stage 114 and the imaging by the imaging device 116 again after the elapse of several hours and perform the measurement of the sample 26 over several days.

The image of the sample 26 captured by the imaging device 116 (hereinafter, captured image) is subjected to image analysis by image analysis software of the PC 13. Hereinafter, the image analysis will be described. FIG. 5 is a diagram showing an example of results of analysis. The image analysis may be, for example, motion detection processing by block matching and detect how much a point set in an image is moved within a predetermined period of time by block matching.

Figure 6:
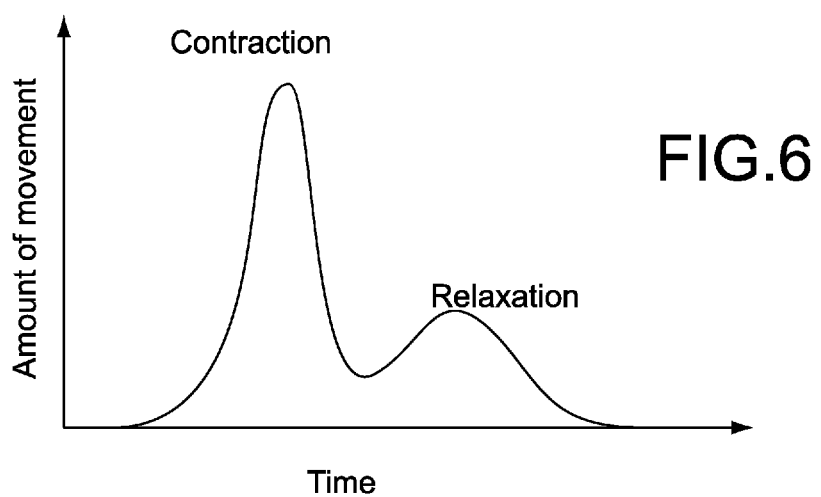
FIG. 6 is a graph as an example obtained based on the results of the image analysis performed by the measurement apparatus.

In the image shown in FIG. 5, the length of a line corresponds to a vector of a movement. This signal is integrated in a target portion to be analyzed, thus obtaining signals of contraction, relaxation, and the like. FIG. 6 is a graph showing the amount of the movement with respect to the time, which has been obtained by the analysis.

When the well 22 unsuitable for measurement is subjected to determination, the results of the image analysis may be used. Specifically, after the imaging performed by the imaging device 116, if the total amount of the movement obtained based on the result of the image analysis for the captured image has a predetermined threshold value or smaller, it can be determined that the pulsations of the sample 26 contained in the well 22 are stopped. In subsequent measurement, the controller 134 can exclude the well 22 from measurement targets.

As described above, in this embodiment, a well 22 unsuitable for measurement is set by the setting unit 133 so that the well 22 does not face the objective lens 115 when the controller 134 controls the stage. Thus, the well 22 unsuitable for measurement is prevented from being imaged by the imaging device 116, and a measurement time can be shortened. Further, since the vibration isolation table 117 prevents vibrations from the outside from being transmitted, the influence due to the vibrations at a time of image analysis is eliminated so that precise analysis can be performed.

(Second Embodiment)

Hereinafter, a measurement apparatus according to a second embodiment will be described. Since the measurement apparatus according to this embodiment has the same configuration as that of the measurement apparatus 1 according to the first embodiment, the description thereof will be omitted.

(Operation of Measurement Apparatus)

Figure 7:
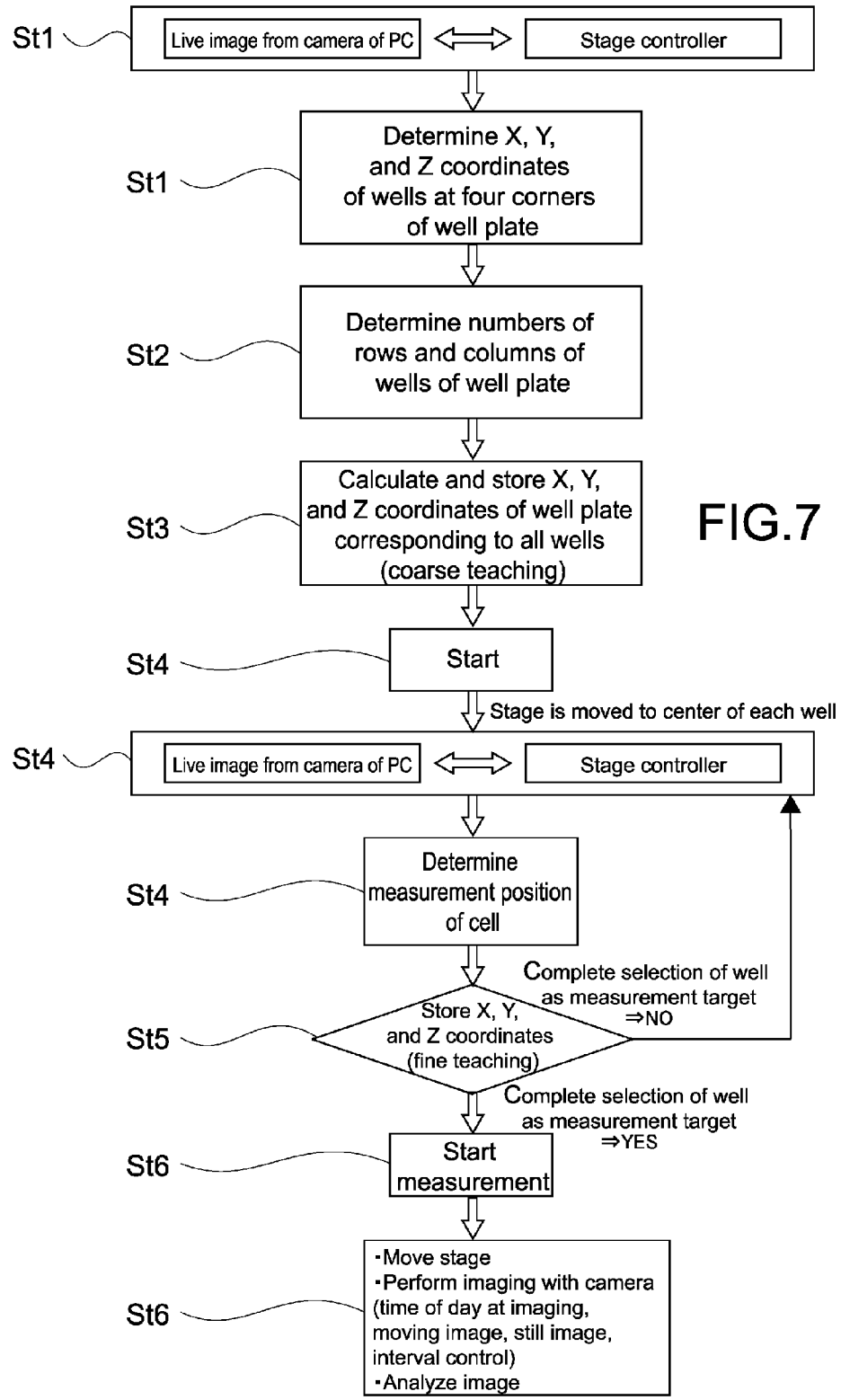
FIG. 7 is a flowchart showing the operation of the measurement apparatus according to the second embodiment.

The operation of the measurement apparatus 1 according to this embodiment will be described. FIG. 7 is a flowchart showing the operation of the measurement apparatus 1. In this embodiment, the operation of determining the positions of the wells 22 in the culture vessel 20 will be executed before the operation of the measurement apparatus 1 described in the first embodiment.

First, a user designates wells 22 at four corners of the culture vessel 20 (St 1). Specifically, the user operates the stage controller 12 while viewing a low-magnification image of a partial area in the culture vessel 20, which is displayed on the display of the PC 13, and focuses the field of view on one of the wells 22 located at the four corners, thus making inputs to the PC 13.

In response to this, the coordinate acquisition unit 131 acquires the position coordinates of the stage 114 at that time and causes the storage unit 132 to store the position coordinates. Similarly, when the user designates the wells 22 at the four corners, the storage unit 132 stores the position of the stage 114 at that time.

Next, the user inputs the array of the wells 22 in the culture vessel 20 (St 2). For example, the numbers of rows and columns of the array of the wells 22 may be input. The coordinate acquisition unit 131 calculates the positions of all the wells 22 in the culture vessel 20 based on position coordinates of the stage 114 that correspond to the wells 22 at the four corners and the array of the wells 22, and the storage unit 132 stores the position coordinates of the stage 114 at which each of the wells 22 falls within the field of view (coarse teaching) (St 3).

After that, the user determines an observation position in each of the wells 22 as in the first embodiment (St 4 to St 6). Here, in this embodiment, since the stage position corresponding to each of the wells 22 are stored in advance in the storage unit 132 as described above, the automatic positioning of the stage 114 is performed as follows.

Figure 8:
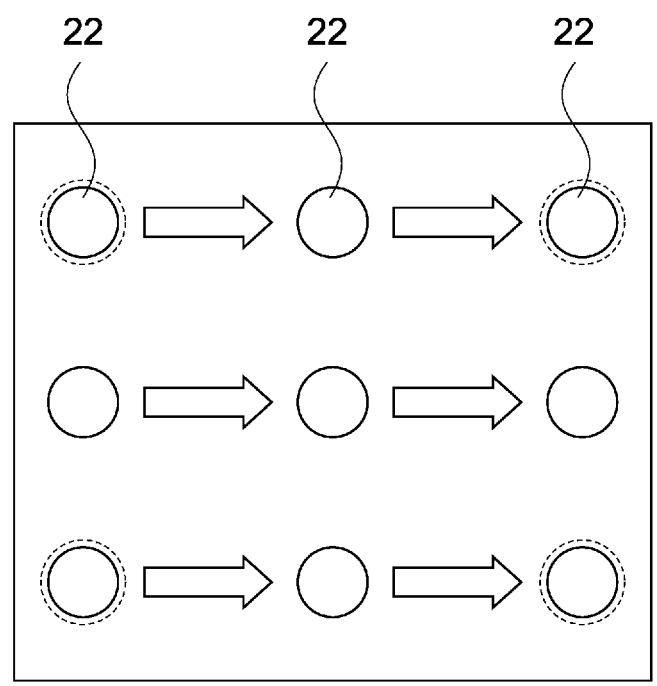
FIG. 8 is a schematic diagram showing the movement control of a stage.

FIG. 8 is a schematic diagram showing the operation of the automatic positioning of the stage 114 by the controller 134. As shown in FIG. 8, when the user makes inputs to the PC 13, the controller 134 moves the stage 114 to the position coordinates stored in the storage unit 132 (movement path is indicated by arrows in FIG. 8). Thus, the user does not need to focus the field of view of the images on one of the wells 22 by using the stage controller 12 while viewing a low-magnification image and can determine the observation position.

When the user makes inputs to the PC 13 again after determining the observation position, the controller 134 moves the stage 114 to the position coordinates corresponding to the next well 22 and being stored in the storage unit 132. Specifically, the user does not need to set the field of view of the images at a lower magnification to search for the next well 22 and can determine the observation position without changing the high magnification of the images.

Thus, the observation positions of all the wells 22 in the culture vessel 20 are determined (St 4). The coordinate acquisition unit 131 acquires the position coordinates of the stage 114 at the respective observation positions and supplies the position coordinates to the storage unit 132 (fine teaching) (St 5). In the case where there are wells 22 unsuitable for measurement as in the first embodiment, the user can make inputs indicating that the wells 22 are unsuitable for measurement to the PC 13. In response to this, the setting unit 133 can delete the position coordinates corresponding to the wells 22 from the storage unit 132. Further, the setting unit 133 can detect the wells 22 unsuitable for measurement based on results of the image analysis or the output of electrodes immersed in the wells 22 in addition to the inputs by the user and delete the position coordinates of the wells 22 from the storage unit 132.

Upon completion of the determination of the observation positions for all the wells 22 in the culture vessel 20, the measurement is started (St 6). The controller 134 acquires the position coordinates of the stage 114, which correspond to the wells 22, from the storage unit 132 and moves the stage 114 so as to be positioned at the position coordinates. Upon completion of the movement of the stage 114, the controller 134 causes the imaging device 116 to capture an image (moving image or still image). In this case, the controller 134 may control the illumination light source 111, the ring aperture 112, and the objective lens 115 at the same time and adjust imaging conditions.

Upon completion of the movement of the stage 114 and the imaging by the imaging device 116 for all the position coordinates stored in the storage unit 132, this measurement is terminated. After that, for example, it is also possible to perform the movement of the stage 114 and the imaging by the imaging device 116 again after the elapse of several hours and perform the measurement of the sample 26 over several days.

Upon completion of the determination of the observation positions for all the wells 22 in the culture vessel 20, the measurement is started. The controller 134 acquires the position coordinates of the stage 114, which correspond to the wells 22, from the storage unit 132 and moves the stage 114 so as to be positioned at the position coordinates. Upon completion of the movement of the stage 114, the controller 134 causes the imaging device 116 to capture an image (moving image or still image). After that, the movement of the stage 114 and the imaging by the imaging device 116 are repeatedly performed. As in the first embodiment, the image analysis can be performed on a captured image.

As described above, in this embodiment, a well 22 unsuitable for measurement is set by the setting unit 133 so that the well 22 does not face the objective lens 115 when the controller 134 controls the stage. Thus, the well 22 unsuitable for measurement is prevented from being imaged by the imaging device 116, and a measurement time can be shortened. Further, since the vibration isolation table 117 prevents vibrations from the outside from being transmitted, the influence due to the vibrations at a time of image analysis is eliminated so that precise analysis can be performed.

Further, in this embodiment, the position coordinates of the stage 114 at which each of the wells 22 falls within the field of view are acquired in advance so that the position coordinates of the stage 114 are automatically controlled when the user determines an observation position in each of the wells 22. Thus, the user does not need to perform an operation of focusing the field of view on each of the wells, which increases convenience of the user.

The present disclosure is not limited to the embodiments described above and can be modified without departing from the gist of the present disclosure.

It should be noted that the present disclosure can employ the following configurations.

(1) A measurement apparatus, including:
an objective lens;
a stage configured to support a sample vessel in which a plurality of wells each containing a sample are arranged and to define relative positions of the sample vessel and the objective lens;
a setting unit configured to determine whether to set each of the plurality of wells to be a measurement target and set the measurement target; and
a controller configured to control the stage such that a well determined to be the measurement target by the setting unit and the objective lens face each other.

(2) The measurement apparatus according to (1), further including a coordinate acquisition unit configured to acquire coordinates of positions of the stage at which each of the plurality of wells faces the objective lens at an observation position thereof, in which
the setting unit is configured to supply, of the coordinates of the positions of the stage, coordinates of a position at which a well determined to be the measurement target faces the objective lens at an observation position thereof, to the controller.

(3) The measurement apparatus according to (1) or (2), in which
the coordinate acquisition unit is configured to acquire coordinates of positions of the stage at which each of the plurality of wells faces the objective lens at a center position thereof, and
the controller controls the stage such that each of the plurality of wells faces the objective lens at the center position thereof.

(4) The measurement apparatus according to any one of (1) to (3), in which
the coordinate acquisition unit is configured to acquire, based on coordinates of positions of the stage at which each of wells at four corners of the sample vessel faces the objective lens at a center position thereof, the wells being designated by a user, and on an array of the plurality of wells in the sample vessel, the coordinates of the positions of the stage at which each of the plurality of wells faces the objective lens at the center position thereof.

(5) The measurement apparatus according to any one of (1) to (4), in which
the setting unit is configured to perform the setting based on a result of image analysis of the sample, the result being imaged via the objective lens.

(6) The measurement apparatus according to any one of (1) to (5), in which
the sample includes a pulsatile cell, and
the setting unit is configured to exclude, from measurement targets, a well containing a pulsatile cell whose pulsations are stopped.

(7) The measurement apparatus according to any one of (1) to (6), further including a vibration isolation table including the objective lens and the stage and being configured to attenuate vibrations from the outside.

(8) A program causing a computer to function as:
a setting unit configured to determine whether to set each of a plurality of wells to be a measurement target and set the measurement target in a sample vessel in which the plurality of wells each containing a sample are arranged; and
a controller configured to control a stage configured to support the sample vessel such that a well determined to be the measurement target by the setting unit and an objective lens face each other.

(9) A measurement method, comprising:
determining, by a setting unit, whether to set each of a plurality of wells to be a measurement target and setting the measurement target in a sample vessel in which the plurality of wells each containing a sample are arranged; and
controlling, by a controller, a stage configured to support the sample vessel such that a well determined to be the measurement target by the setting unit and an objective lens face each other.

(10) A measuring apparatus comprising:
a stage configured to support a vessel including a plurality of samples, each of the samples contained within a respective well;
an image device configured to capture an image of at least one sample; and
a processor communicatively coupled to a stage controller and configured to determine which of the plurality of samples are to be imaged by the image device.

(11) The measuring apparatus according to (10), wherein the processor is configured to determine which of the plurality of samples are not to be imaged.

(12) The measuring apparatus according to of any one of (10) or (11), wherein the processor is configured to provide instructions causing the stage controller to move the stage or the image device to align the image device with the at least one sample that has been determined to be imaged.

(13) The measuring apparatus according to of any one of (10) to (12), wherein the processor is configured to determine which of the plurality of samples is to be imaged based on image analysis.

(14) The measuring apparatus according to of any one of (10) to (13), wherein the processor is configured to perform the image analysis by:
determining an amount of movement of the sample within the respective well by comparing previous images of the sample in the well; and
determining the sample is not to be further imaged if the amount of movement is below a predetermined threshold.

(15) The measuring apparatus according to of any one of (10) to (14), wherein the processor is configured to determine a location for each of the plurality of samples on the vessel by:
prompting a user to align a least one well with the image device;
determining an observation position within each well; and
recording the location relative to the vessel of each of the observation positions aligned with the image device.

(16) The measuring apparatus according to of any one of (10) to (15), wherein the processor is configured to determine the location for each of the plurality of samples on the vessel by:
prompting the user for a number of rows and columns of the wells included within the vessel; and
determining the locations of each of the samples based on the known locations of wells aligned with the image device and the number of rows and columns of the vessel.

(17) The measuring apparatus according to of any one of (10) to (16), wherein the processor is configured to prompt the user to align the wells located on four corners of the vessel with the image device.

(18) The measuring apparatus according to of any one of (10) to (17), wherein the processor is configured to:
determine the observation position for each of the plurality of samples by detecting within each well where the sample is visually active; and
control movement of the stage to align each sample with the image device based on the determined observation position.

(19) The measuring apparatus according to of any one of (10) to (18), wherein at least one of the wells includes two samples and the processor is configured to determine the observation point by determining which of the two samples is more visually active.

(20) The measuring apparatus according to of any one of (10) to (19), wherein the processor is configured to determine that the well has two observation points when both of the samples included within a well have a visual activity that is greater than a predetermined threshold.

(21) The measuring apparatus according to of any one of (10) to (20), wherein the processor is configured to determine which of the plurality of samples is to be imaged based on an input from a user.

(22) The measuring apparatus according to of any one of (10) to (21), further comprising a vibration isolation table configured to prevent vibrations external to the measuring apparatus from being transmitted to at least one of the stage or the image device.

(23) A method of measuring at least one sample included within respective wells of a vessel, the method comprising:
determining an observation position for each of the plurality of samples;
determining which of the plurality of samples is to be imaged by an image device; and
imaging the samples determined to be imaged using the image device.

(24) The method according to (23), further comprising:
determining which of the plurality of samples is not to be imaged by the image device; and
refraining from imaging the samples that are not to be imaged.

(25) The method according to any one of (23) or (24), wherein determining the observation positions includes:

determining coordinates of wells at four corners of the vessel;
determining a number of rows and columns of wells within the vessel;
calculating coordinates for each of the wells based on the known locations of the wells at the four corners and the number of rows and columns of the vessel; and
identifying a portion of each well as the observation position where the respective sample is visually active above a predetermined threshold.

(26) The method according to any one of (23) to (25), wherein the coordinates of the wells at the four corners and the number of rows and columns is provided by a user responsive to a prompt.

(27) The method according to any one of (23) to (26), wherein determining which if the plurality of samples to be imaged includes:
determining at least one movement vector from portions of the sample within the respective well by comparing previous images of the portions of sample in the well; and
determining the sample is not to be further imaged if an average of the at least one movement vector for each of the portions is below a predetermined threshold.

(28) The method according to any one of (23) to (27), wherein determining which if the plurality of samples to be imaged includes receiving an indication from a user.

(29) The method according to any one of (23) to (28), further comprising moving a stage holding the vessel or the image device to align the image device with the at least one sample that has been determined to be imaged.

(30) A machine-accessible medium having instructions stored thereon that are configured when executed to cause a machine to at least:
determine an observation position for each of a plurality of samples included within respective wells of a vessel;
determine which of the plurality of samples is to be imaged by an image device; and
image the samples determined to be imaged using the image device.

(31) The machine-accessible medium according to (30), wherein the observation position includes coordinates relative to the vessel that correspond to which sample is to be aligned with the image device.

(32) The machine-accessible medium according to any one of (30) or (31), further comprising instructions stored thereon that are configured when executed to cause a machine to at least:
determine an amount of activity of the sample within each of the wells by comparing previous images of the sample in the well; and
determining the sample is not to be further imaged if the amount of activity is below a predetermined threshold.

(33) The machine-accessible medium according to any one of (30) to (32), further comprising instructions stored thereon that are configured when executed to cause a machine to at least move a stage holding the vessel or the image device to align the image device with the at least one sample that has been determined to be imaged.

(34) The machine-accessible medium according to any one of (30) to (33), further comprising instructions stored thereon that are configured when executed to cause a machine to at least image one sample at a time.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST 11 main body
12 stage controller
13 PC
20 culture vessel
22 well
22 all wells
114 stage
115 objective lens
117 vibration isolation table
131 coordinate acquisition unit
132 storage unit
133 setting unit
134 controller

The invention claimed is:

1. A measuring apparatus comprising:
a stage configured to support a vessel including a plurality of samples, each of the samples contained within a respective well of a plurality of wells;
an image device configured to capture an image of at least one sample; and
a processor communicatively coupled to a stage controller and configured to determine which of the plurality of samples are to be imaged by the image device, based on image analysis of determining an amount of movement of the sample within the respective well by comparing previous images of the sample in the well, and determining the sample is not to be further imaged if the amount of movement is below a predetermined threshold,
wherein at least one of the plurality of wells includes two samples and the processor is configured to determine an observation position by determining which of the two samples is more visually active.

2. The measuring apparatus of claim 1, wherein the processor is configured to determine a location for each of the plurality of samples on the vessel by:
prompting a user to align the at least one of the plurality of wells with the image device;
determining the observation position within each well; and
recording the location relative to the vessel of each of the observation positions aligned with the image device.

3. The measuring apparatus of claim 2, wherein the processor is configured to determine the location for each of the plurality of samples on the vessel by:
prompting the user for a number of rows and columns of the wells included within the vessel; and
determining the locations of each of the samples based on the known locations of wells aligned with the image device and the number of rows and columns of the vessel.

4. The measuring apparatus of claim 2, wherein the processor is configured to prompt the user to align the wells located on four corners of the vessel with the image device.

5. The measuring apparatus of claim 2, wherein the processor is configured to:
determine the observation position for each of the plurality of samples by detecting within each well where the sample is visually active; and control movement of the stage to align each sample with the image device based on the determined observation position.

6. A measuring apparatus comprising:
a stage configured to support a vessel including a plurality of samples, each of the samples contained within a respective well of a plurality of wells;
an image device configured to capture an image of at least one sample; and
a processor communicatively coupled to a stage controller and configured to determine which of the plurality of samples are to be imaged by the image device, based on image analysis of determining an amount of movement of the sample within the respective well by comparing previous images of the sample in the well, and determining the sample is not to be further imaged if the amount of movement is below a predetermined threshold,
wherein the processor is further configured to determine that at least one of the plurality of wells has two observation points in an event both of the samples included within the at least one of the plurality of wells have a visual activity greater than a predetermined threshold.

7. The measuring apparatus of claim 1, wherein the processor is configured to determine which of the plurality of samples is to be imaged based on an input from a user.

8. The measuring apparatus of claim 1, further comprising a vibration isolation table configured to prevent vibrations external to the measuring apparatus from being transmitted to at least one of the stage or the image device.

9. A method of measuring at least one sample included within respective wells of a vessel, the method comprising:
determining an observation position for each of the plurality of samples;
determining which of the plurality of samples is to be imaged by an image device, wherein determining which of the plurality of samples to be imaged includes determining at least one movement vector from portions of the sample within the respective well by comparing previous images of the portions of sample in the well, and determining the sample is not to be further imaged if an average of the at least one movement vector for each of the portions is below a predetermined threshold; and
imaging the samples determined to be imaged using the image device.

10. The method of claim 9, further comprising:
determining which of the plurality of samples is not to be imaged by the image device; and
refraining from imaging the samples that are not to be imaged.

11. The method of claim 9, wherein determining the observation positions includes:
determining coordinates of wells at four corners of the vessel;
determining a number of rows and columns of wells within the vessel;
calculating coordinates for each of the wells based on the known locations of the wells at the four corners and the number of rows and columns of the vessel; and
identifying a portion of each well as the observation position where the respective sample is visually active above a predetermined threshold.

12. The method of claim 11, wherein the coordinates of the wells at the four corners and the number of rows and columns are provided by a user responsive to a prompt.

13. The method of claim 9, wherein determining which of the plurality of samples to be imaged includes receiving an indication from a user.

14. The method of claim 9, further comprising moving a stage holding the vessel or the image device to align the image device with the at least one sample that has been determined to be imaged.

* * * * *